United States Patent [19]

Maasböl

[11] 4,370,331

[45] Jan. 25, 1983

[54] L-GLAUCINE CONTAINING COMPOSITION FOR COUGH RELIEF

[75] Inventor: Alfred G. Maasböl, Hamburg, Fed. Rep. of Germany

[73] Assignee: Karl O. Helm Aktiengesellschaft, Hamburg, Fed. Rep. of Germany

[21] Appl. No.: 151,197

[22] Filed: May 16, 1980

Related U.S. Application Data

[63] Continuation of Ser. No. 895,718, Apr. 12, 1978, abandoned.

[30] Foreign Application Priority Data

Apr. 18, 1977 [DE] Fed. Rep. of Germany ....... 2717062

[51] Int. Cl.$^3$ .............................................. A61K 31/47
[52] U.S. Cl. .................................................... 424/258
[58] Field of Search .......................................... 424/258

[56] References Cited

U.S. PATENT DOCUMENTS 2,397,903  4/1946  Puetzer ............................ 544/327
2,641,010  6/1953  Barber ......................... 260/567.6 P

OTHER PUBLICATIONS

Farmatsiya (Sofia), 12 (4), 17–21 (1962)–N. Donev, Pharmacology of Glaucine.
The Plant Alkaloids–Henry (1913)–pp. 258–259.
Chem. Abst. 76, 135,836(s) (1972)–Angelova et al.
Chem. Abst. 78, 88,550(y) (1973)–Bubeva-Ivanova et al.
Chem. Abst. 84, 159,725(w) (1976)–Aleshinskaya.
Chem. Abst. 90, 43,806(t) (1979)–Maasboel.
Chem. Abst. 93, 101,493(p) (1980)–Wang.

*Primary Examiner*—Douglas W. Robinson
*Attorney, Agent, or Firm*—Michael J. Striker

[57] ABSTRACT

An antitussive composition comprising a pharmaceutically acceptable carrier and from about 4 to about 99 percent by weight of a glaucine compound selected from the group consisting of l-glaucine, d,l-glaucine, the physiologically acceptable salts thereof and mixtures thereof.

22 Claims, No Drawings

L-GLAUCINE CONTAINING COMPOSITION FOR COUGH RELIEF

This is a continuation of application Ser. No. 895,718, filed Apr. 12, 1978 now abandoned.

In bronchial and pulmonary illnesses a cough reflex occurs due to the efforts to free the breathing tract from mechanical or pathological irritations. A medical suppression of this reflex is indicated when a dry, irritated cough occurs, as it does for example in asthma, whooping cough, tubercolosis, lung cancer and the like. The cough-suppressive effect can act on sensory nerves, on the cough centre or in the autonomous nerve system. The preferred substances are those which act on the cough centre.

The best known cough-inhibiting substance is codeine, which acts centrally, but this substance when given orally has a slight addictive effect because demethylation in the organism produces morphine. This result is quite important when codeine is injected. The most important side effects in codeine therapy are constipation and depression of the breathing action, and for this reason the application of codeine is in many cases contra-indicated or at least entails disadvantages. A further objection to codeine is that its manufacture requires a plantationwise cultivation of opium poppies.

It is known that the alkaloid d-glaucine, which is structurally related to codeine and can be isolated from the flowers of the yellow poppy, can be applied in cough therapy. Glaucine has the chemical structure:

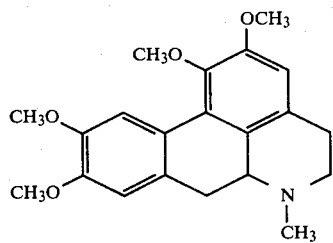

A difficulty arises in that the poppy flower contains at least four other alkaloids, whose separation from d-glaucine is extremely difficult.

According to Franck and Tietze: "Angewandte Chemie" (1967), pages 815 and 816, the compound d, l-glaucine can be synthesized, starting from papaverine, by the oxidative ring-closing reaction of laudanosoline. But the glaucine synthesized by this method contains considerable quantities of unidentified impurities, which it has not hitherto been possible to separate. In my own research I have found that the main impurity involved is the substance 1-(N,N-dimethylaminoethyl)-3,4,6,7-tetramethoxyphenanthrene, which is apparently produced by Hofman degradation. The substance crystallizes out with the glaucine salt. Due to its phenanthrene structure and to the often sympathomimetically active dimethylaminoethyl group this glaucine should be regarded as inadvisable for therapeutic use.

The object of the present invention is to provide a medicine with anti-cough effect, and to provide improved anti-cough active substances which, even when given orally, have a pronounced central cough-inhibitive effect which lasts as long as possible, the substances not being addictive and being largely free from the undesired gastro-intestinal side effects of the known products.

It has now been found that l-glaucine has an anti-cough effect which is in some ways superior to the effect produced by d-glaucine, and that the combined application of l-glaucine and d-glaucine in a certain weight ratio produces an unexpected improvement in the cough-inhibitive effectiveness.

In solving this problem the novel anti-cough drug is characterized, according to the invention, by a therapeutically effective content of l-glaucine or its physiologically unobjectionable salts with inorganic or organic acids.

The new medicine is outstanding compared to the known anti-cough medicines containing codeine or d-glaucine in that it is free from spasm-inducing side effects in the intestinal region and in that, compared to preparations containing d-glaucine, it has an unexpectedly increased anti-cough effect.

In a further development of the invention the medicine can also contain an at most equimolar quantity, based on the total content of l-glaucine and l-glaucine salts, of d-glaucine and/or its physiologically unobjectionable salts with inorganic or organic acids.

The combined application of l-glaucine and d-glaucine and their salts, within the molar ratios given above, unexpectedly provides a still further improvement of the anti-cough effect not only compared with the same quantity of l-glaucine but also, and even more, compared with the considerably less effective d-glaucine.

In a preferred version of the invention the medicine can contain embonic acid salts of l-glaucine and, if desired, of d-glaucine. This considerably prolongs the anti-cough effect, without delaying the beginning of the effect.

Also claimed in the invention is the hitherto unknown glaucine embonate, both in its racemic form and in the form of separated optical isomers.

The l-glaucine required for the new medicine can be manufactured synthetically by the process described at the beginning, that is by the oxidative ring-closing reaction of laudanosoline. But the applicant has found that the glaucine synthesized in this way contains considerable quantities of byproducts which have not hitherto been regarded as impurities and which crystallize out with the glaucine salt. In our own researches we have found that the substance mainly involved is 1-(N,N-dimethylaminoethyl)-3,4,6,7-tetramethoxyphenanthrene. The action of this substance in a medicine must be excluded, due to its phenanthrene structure and due to the effect of the dimethylaminoethyl group. We therefore had to develop a process for manufacturing a purified glaucine.

A further problem tackled in the present invention is therefore to develop a process for manufacturing a purified glaucine, the solution according to the invention being characterized in that starting out from the impure glaucine manufactured synthetically from laudanosoline, the free base is separated from the accompanying 1-(N,N-dimethylaminoethyl)-3,4,6,7-tetramethoxyphenanthrene by fractional crystallization from an organic solvent, preferably ethyl alcohol or acetic acid ethyl ester, after which the purified galucine can if desired be separated into its optical isomers.

Finally within the frame of the invention there is also claimed a process for manufacturing purified glaucine, in which tetrahydroxyaporphine made from laudanosoline is methylated to give glaucine, the process being characterized in that the glaucine in the reaction mixture of the methylation stage is extracted with dilute sulphuric acid and is then isolated from the sulphuric acid phase after separation of the precipated solids.

By this method it is possible to manufacture, in a simple manner and without noticeably impairing the yield, a glaucine which is free from undesired by-products mentioned above.

In what follows there will be described in greater detail the manufacture of purified l-glaucine and glaucine salts, as well as the therapeutic effectiveness of these substances, on the basis of examples and comparative tests.

EXAMPLE 1

Manufacture of purified l-glaucine

To 225 g (0.6 Mol) of papaverine hydrochloride in 2 liters of 50% aqueous methyl alcohol there was added a solution of 30 g of sodium hydroxide in 300 ml of water. The resulting precipitate was filtered off and dried at 60° C. for 20 hours. The product was 201 g of papaverine base with a melting point of 144° to 146° C. (yield 98%).

200 g of the papaverine base was dissolved in 200 ml of methyl alcohol. To the solution there was added 120 ml of methyl iodide and the whole heated to boiling during 6 hours. After cooling, the crystallized product was filtered off and dried. The product was 280 g of papaverine methiodide with a melting point of 127° to 129° C. (yield 97%).

200 g (0.4 Mol) of the papaverine methiodide was suspended in 2 liters of a 10% aqueous methyl alcohol and to this mixture there was added sodium borhydride until complete solution was obtained and the yellow-orange colouration had disappeared. The resulting solution was poured into 12 liters of water and the resulting white precipitate was filtered off and dried. The product was 230 g of laudanosine with a melting point of 113° to 115° C. (yield 78%).

121 g (0.34 Mol) of the laudanosine was heated in 600 ml of 40% hydrobromic acid for about 10 hours, until all the methyl bromide had been given off. After cooling the solution, the crystalline product was separated. The product was 100 g of laudanosoline hydrobromide with a melting point of 230° C. (yield of 77%).

98 g (0.26 Mol) of laudanosoline hydrobromide was dissolved in 1.2 liters of a 50% aqueous methyl alcohol at 80° C. After complete solution the solution was cooled down to 6° C. by adding ice, after which there was added a filtered solution, which had also been cooled to 6° C., of 100 g (0.62 Mol) of iron (III) chloride in 500 ml of 50% aqueous methyl alcohol. After one minute there was added 1.5 liters of concentrated hydrochloric acid and the solution was allowed to stand at room temperature. The precipitated grey-brown crystals were filtered off, washed with acetone and dried. The product was 43 g of tetrahydroxyaporphine hydrochloride showing a melting point of 242° to 244° C. (yield 50%).

6 g (0.018 Mol) of tetrahydroxyaporphine hydrochloride was dissolved in 840 ml of methyl alcohol, with warming. Separate from this, 21.6 g (0.126 Mol) of trimethylphenylammonium chloride in methyl alcohol was reacted with a solution of 8.5 g (0.15 Mol) of KOH in methyl alcohol. After filtering off the precipitated potassium chloride, the filtrate was made up to 840 ml with methyl alcohol. The two solutions were then mixed together slowly under a protective gas, and was added slowly in the course of 6 hours to anisol heated to 100° C., the methyl alcohol distilling off. After completion of the addition the solution was cooled and a black, amorphous residue was removed by filtering. The resulting dark green filtrate was evaporated under vacuum until dry. To the residue there was added 5 ml of ethanol, 15 ml hydrobromicacid and 20 ml ethyl acetate. From the resulting mixture a product crystallized out and was filtered off and dried. The product was 5.5 g of d,l-glaucine hydrobromide with a melting point of 235° C. (with decomposition) (yield 67%).

A thin-layer chromatograph showed that the d,l-glaucine hydrobromide obtained in this way contained about 10% of 1-(N,N-dimethylaminoethyl)-3,4,6,7-tetramethoxyphenanthrene. 60 g of the d,l-glaucine hydrobromide was dissolved in 200 ml 50% aqueous ethylalcohol and treated with an excess of 8.5 g potassium hydroxide in 50 ml of water.

The resulting mixture was shaken with about 500 ml of chloroform to extract the free d,l-glaucine base. The separated organic phase was dried over anhydrous sodium sulphate and filtered. After evaporating off the solvent 50 g of an oily residue was obtained and this was recrystallized from 75 ml of ethyl acetate. After filtering and drying there was obtained 30.4 g of d,l-glaucine base showing a melting point of 128° to 130° C. After repeated recrystallization from further 100 ml portions of ethyl acetate, there was obtained 25.15 g of d,l-glaucine base with a melting point of 138° to 140° C. By making a thin-layer chromatograph it was determined that this contained less than 0.1% impurities.

After recrystallizing the combined residues from ethyl alcohol there was obtained about 5 g of 1-(N,N-dimethylaminoethyl)-3,4,6,7-tetramethoxyphenanthrene with a melting point of 248° to 250° C. and a molecular weight, determined by mass spectrometry, of 369.

NMR spectrum: 9.13(s, 1), 7.88(d, 1), 7.66(d,1), 7.46(s,2) 3.97(s,3), 3.93(s,6),3.86(s,3),3.44-3.14(m,4) 2.73(s,3), 2.52(s,3).

To separate the isomers, 5.09 g (0.014 Mol) of d,l-glaucine was dissolved in 70 ml of ethyl alcohol and the solution reacted with a solution of 2.2 g (0.014 Mol) of d-tartaric acid in 70 ml of ethyl alcohol (50° C.). Slow cooling resulted in a fine crystalline precipitate, which was filtered off, washed with ether and dried. The product was 3.6 g of l-glaucine-d-bitartrate with a melting point of 210° to 212° C. and a specific rotation in water of −26° (yield 93%).

The still impure l-glaucine-d-bitartrate was reacted with an aqueous solution of sodium hydroxide and extracted with ether. After evaporating the solvent, the residue was dissolved in 50 ml of ethyl alcohol and reacted with a solution of 1.15 g of d-tartaric acid in 50 ml of ethyl alcohol. After separation there was obtained 3.39 g of l-glaucine-d-bitartrate showing a melting point of 212° to 215° C. and a specific rotation in water of −32°. The specific rotation of the l-glaucine base in ethyl alcohol was −101° (94% optical purity).

2.48 g of l-glaucine was reacted in 15 ml of ethyl alcohol with a small excess of 48% hydrobromic acid. After separation there was obtained 2.78 g of l-glaucine hydrobromide with a melting point of 235° C. (with decomposition) (yield 98.5%).

From the mother liquors of the first and second d-bitartrate crystallizations there was obtained, after evaporation, a greenish residue, which was dissolved in 20 ml of water, treated with aqueous sodium hydroxide and then extracted with 250 ml of ether. After drying and filtering, the solvent was evaporated, giving 1.67 g of d-glaucine with a melting point of 120° C. The specific rotation in alcohol was 104.6°. By reacting this product with hydrobromic acid there was obtained a d-glaucine hydrobromide with a melting point of 235° C. (with decomposition). The d-glaucine obtained by methylation from d-boldine showed a specific rotation in ethyl alcohol of +115°.

EXAMPLE 2

To make l-glaucine hydrochloride, a quantity of l-glaucine was dissolved in a little methyl alcohol and to the solution there was added a small excess of concentrated hydrochloric acid. To the resulting voluminous precipitate there was added ethyl acetate, giving whitish to pink crystals. After filtering, washing with acetone and drying there were obtained white to pink fine crystals of l-glaucine hydrochloride with a melting point of 232° to 233° C.

EXAMPLE 3

For making l-glaucine hydroiodide, a quantity of l-glaucine was dissolved in 2 n hydrochloric acid and the solution reacted with saturated potassium iodide solution. The resulting crystalline precipitate was recrystallized from a mixture of methyl alcohol and ether. This gave a crystalline, yellowish glaucine hydroiodide with a melting point of 238° C.

EXAMPLE 4

For making l-glaucine embonate, 841 mg of l-glaucine was reacted in 10 ml of dimethyl formamide with 459 mg of embonic acid. After heating to complete solution, the mixture was poured into 100 ml of water and the precipitated product filtered and dried. The product was 1.32 g of powdery, slightly brownish l-glaucine embonate with a melting point of 189° to 192° C. (yield 100%).

EXAMPLE 5

For making d,l-glaucine embonate, a mixture of 1.42 g of d,l-glaucine and 0.78 g of embonic acid was dissolved in 20 ml of dimethyl formamide and the resulting brown solution was introduced into 400 ml of water. The resulting slightly brownish precipitate was filtered off, washed with water and dried. The product was 1.75 g of d,l-glaucine embonate with a melting point of 188° to 190° C. (yield 80%).

Analysis: $C_{65}H_{66}N_2O_{14}$; calculated: C 71.02%, H 6.05%, N 2.55%; found: C 69.36%, H 5.98, N 2.52%.

EXAMPLE 6

For making d,l-glaucine tartrate, 355 mg (1 Mol) of d,l-glaucine in 10 ml of ethyl alcohol was reacted with 150 mg of d,l-tartaric acid in 10 ml of ethyl alcohol at 50° C. After cooling the solution there was obtained 220 mg of optically inactive d,l-glaucine-d,l-tartrate with a melting point of 215° C. (yield 97%).

EXAMPLE 7

Coated pills with an anti-cough effect were made of the following components:

| Core: | l-glaucine hydrobromide | 20 mg |
| | lactose | 60 mg |
| | starch | 40 mg |
| | talcum | 10 mg |
| | | 130 mg |
| Coating: | gum arabic | 4.5 mg |
| | talcum | 35 mg |
| | crystallized sugar | 80 mg |
| | white wax | 0.1 mg |
| | red dye | 0.4 mg |
| | | 120 mg |

EXAMPLE 8

For making capsules with long-period anti-cough effect, stretch-capsules of hard gelatin were each filled with 160 mg of a mixture of the following components:

| d,l-glaucine hydrochloride | 10 mg |
| --- | --- |
| d,l-glaucine embonate | 25 mg |
| lactose | 60 mg |
| starch | 60 mg |
| magnesium stearate | 5 mg |
| | 160 mg |

EXAMPLE 9

For making a syrup with an anti-cough effect the following components were mixed together:

| l-glaucine hydrobromide | 133 mg |
| --- | --- |
| saccharose | 20 mg |
| sorbitol | 45 mg |
| citric acid | 125 mg |
| p-hydroxybenzoic methyl ester | 100 mg |
| aroma (essence of sweet oranges) | 1.5 g |
| distilled water, up to | 100 g |

Comparative test 1

In order to compare the anti-cough effectiveness of codeine phosphate with the effectiveness of the different isomers of glaucine hydrobromide, the testing method of Friebel and Reichle was used. 60 guinea pigs with weights between 200 and 300 g were divided up into ten groups of different sizes. Before administering the active substance, each animal was subjected, on the same day as the day of test with the active substance, for a period of 8 minutes to an aerosol of 20% citric acid, the animal being confined in a chamber at constant air pressure. During this control test the number of cough pulses was counted with the help of a pressure transmitter. From these measurements an average control value for each group was calculated. After this preliminary control test, there was given subcutaneously to each animal of each group a suspension of the active substance in 1% sodium carboxymethyl cellulose. After 30 minutes each animal was again exposed in the test chamber for 8 minutes to the aerosol of 20% citric acid and the number of cough pressure pulses recorded. The different active substances were administered in increasing doses ranging from 3 mg/kg to 100 mg/kg of body weight. Altogether eight different doses were given. The results were expressed as percent deviation from the average control value for the group on the same day, the deviation being entered in a diagram against the logarithm of the dose administered. From the resulting effectiveness curve, based on the logarithm of the dose, the coefficient of correlation and the ED$_{50}$ were calculated for each active substance, by the regression analysis method of Downie and Heath (1965). The values obtained for codeine phosphate, for d-glaucine hydrobromide, for d,l-glaucine hydrobromide and for l-glaucine hydrobromide thirty minutes after administering the active substance are summarized in Table I.

TABLE I

| Active substance | Number of animals | Correlation coeff.* | Rising slope of curve | ED$_{50}$ mg/kg |
|---|---|---|---|---|
| Codeine phosphate | 41 | −0.3956 | −67.4 | 20.6 |
| d-glaucine hydrobromide | 59 | −0.5340 | −60.8 | 54.0 |
| l-glaucine hydrobromide | 38 | −0.6867 | −70.96 | 31.2 |
| d,l-glaucine hydrobromide | 25 | −0.4874 | −57.8 | 27.2 |

*statistically significant ($p < 0.01$) for each active substance

These results show that l-glaucine hydrobromide has a considerably lower effective dose ED$_{50}$ value compared to d-glaucine hydrobromide, and that surprisingly the d,l-glaucine hydrobromide has an even lower ED$_{50}$ value than l-glaucine hydrobromide.

Comparative test 2

One of the most unpleasant side effects of anti-cough medicine containing codeine is constipation and the occurrence of intestinal spasms. A model test for determining the effects of anti-cough active substances on intestinal motility and on the evacuation action of the stomach-intestinal tract of mice was therefore made. After subcutaneous injection of the active substance, each animal was given, through a throat probe, a 10% suspension of carbon in a 5% aqueous slurry of gum arabic. Two hours later the intestine was sectioned and the distance of stomach coecum measured, and also the distance travelled by the carbon, which was expressed as percent of intestine length.

TABLE II

| Active substance | Dose mg/kg | Number of animals | Distance travelled average % | Standard deviation % |
|---|---|---|---|---|
| CONTROL | | 40 | 74.3 | 3.6 |
| codeine phosphate | 3 | 7 | 70.4 | 3.5 |
| | 10 | 18 | 74.3 | 2.4 |
| | 30 | 17 | 34.8* | 9.5 |
| | 100 | 18 | 20.6* | 4.5 |
| d-glaucine hydrobromide | 10 | 18 | 74.6 | 2.5 |
| | 30 | 18 | 80.1 | 2.6 |
| | 100 | 18 | 36.4* | 4.9 |
| l-glaucine hydrobromide | 3 | 8 | 74.3 | 6.3 |
| | 10 | 8 | 94.3* | 2.0 |
| | 30 | 8 | 85.4 | 4.3 |
| | 100 | 8 | 51.8* | 10.6 |

*significantly different from the control value ($p < 0.05$).

The effects of codeine phosphate, of d-glaucine hydrobromide and of l-glaucine hydrobromide on intestinal motility were determined at different doses. For each dose the average value was calculated for a sufficient number of animals. The results of these tests are shown in Table II above.

These results show that l-glaucine hydrobromide, in contrast to d-glaucine hydrobromide and codeine phosphate, administered in a dose of 10 mg/kg resulted in a significant increase in intestinal activity. And even when the dose of l-glaucine hydrobromide is increased to 30 mg/kg and 100 mg/kg, the intestinal motility is considerably more than the corresponding values for d-glaucine hydrobromide and codeine phosphate.

Comparative test 3

Experiments were conducted in vitro to determine the effects of different active substances on the smooth muscles of isolated guinea pigs intestine samples suspended in a bath. After adding to the bath different doses of the active substances, the contractive force of the muscle material was recorded. It was found that codeine at molar concentrations between $1 \times 10^{-5}$ and $32 \times 10^{-5}$ produces contractions which depend on the dose. d-glaucine showed a dose-dependent increase of spontaneous activity and tone at molar concentrations between $1 \times 10^{-5}$ and $8 \times 10^{-5}$. On the other hand, using l-glaucine at molar concentrations between $1 \times 10^{-5}$ and $8 \times 10^{-5}$, a reduction in spontaneous activity and no increase in tone were observed. This shows that l-glaucine, in contrast to d-glaucine and codeine, has no spasmogenic activity.

In further tests it was investigated in what concentrations the active substances being compared suppress spasms induced in isolated guinea pig intestine by carbachol or histamine. It was found that both codeine and d-glaucine are effective against carbachol or histamine at a molar concentration of $1 \times 10^{-3}$ or $4 \times 10^{-5}$. On the other hand d,l-glaucine was effective against histamine at molar concentrations of only $4 \times 10^{-8}$ to $4 \times 10^{-6}$ and against carbachol at molar concentrations of only $4 \times 10^{-7}$.

Comparative test 4

In a further series of tests the effects of different doses of codeine phosphate in suppressing contractions induced in isolated guinea pig intestines by electric voltages were tested. For this purpose one electrode was immersed in the solution surrounding the intestinal preparation. The second electrode was connected to the preparation at the attachment point. Alternating current pulses were applied for 5 seconds and it was found that the resulting contracting reflex is reduced by adding active substance. The results of the tests are shown in Table III.

TABLE III

| Active Substance | Molar Concentration | | | | | | | |
|---|---|---|---|---|---|---|---|---|
| | $4 \times 10^{-6}$ | $5 \times 10^{-6}$ | $8 \times 10^{-6}$ | $1 \times 10^{-5}$ | $2 \times 10^{-5}$ | $4 \times 10^{-5}$ | $6 \times 10^{-5}$ | $8 \times 10^{-5}$ |
| codeine phosphate | — | 85 | — | 49 | 36 | — | — | — |
| | — | 51 | — | 49 | 52 | 58 | — | — |
| d-glaucine hydrobromide | — | — | — | 77 | 74 | 44 | — | — |
| | — | — | — | 95 | 79 | 36 | — | — |
| l-glaucine hydrobromide | — | — | — | 71 | 64 | 24 | — | 7 |
| | — | — | — | 74 | 32 | 23 | — | — |
| d,l-glaucine hydrobromide | — | — | — | 63 | 48 | 8 | — | — |
| | 81 | — | 63 | — | — | — | — | — |

These results show that codeine phosphate at a molar concentration of about $10^{-5}$ suppresses by about 50% the electrically induced contraction reflexes. But increased codeine doses do not result in increased suppression because the spontaneous activity induced by the codeine phosphate itself increases the contractions. It was found that d-glaucine hydrobromide at a dose of $4 \times 10^{-5}$ suppresses electrically induced contraction reflexes. But at higher concentrations the increasing spontaneous activity prevents any distinguishing between direct production and electric production of the activity. Using l-glaucine hydrobromide, it was found that at a concentration of $4\times10^{-5}$ the electrically induced spasms are more effectively suppressed, compared to what is obtained using d-glaucine hydrobomide. At a concentration of $8\times10^{-5}$ of l-glaucine hydrobromide the electrically induced contractions are suppressed even more effectively. Using d,l-glaucine hydrobromide it was found possible at concentrations of $4\times10^{-5}$ to $6\times10^{-5}$ to suppress the electrically induced spasms practically completely, without at the same time inducing any spontaneous activity. In comparing the values shown in the table it should be observed that when the d,l-glaucine hydrobromide is at the concentration of $4\times10^{-5}$, the d-glaucine hydrobromide and the l-glaucine hydrobromide are each at a molar concentration of $2\times10^{-5}$.

Comparative test 5

In a series of tests conducted by the method of Domenjoz, the effects of the different active substances on the coughing centre was examined by electrical stimulation of the upper laryngeal nerves of anaesthetized cats. Electrical stimulation of the nerve produces a coughing reflex and the intention is to reduce this by intravenous injection of the active substance. The minimal effective dose MED is determined by increasing the dose from 0.1 mg/kg of body weight up to 0.3 mg/kg, 1.0 mg/kg, 3.0 mg/kg and 6.0 mg/kg, until the dose is sufficient for completely suppressing the coughing reflex.

In these tests each animal was given, on the one hand, codeine and, on the other hand, at sufficient time intervals also glaucine, so that the ratio of the minimal effective doses of glaucine and codeine can be deduced. Table IV shows the minimal effective doses MED and also the observed duration of cough suppression.

TABLE IV

| Active Substance | MED mg/kg | Duration minutes |
|---|---|---|
| Codeine phosphate | 6 | 18–54 |
| d-glaucine hydrobromide | 1 | 5–39 |
| d,l-glaucine hydrobromide | 1 | 44–62 |

These results show that both the d-glaucine hydrobromide and the d,l-glaucine hydrobromide completely suppress the coughing reflex already at a dose of 1 mg/kg of body weight. The dose of codeine phosphate required for this is 6 mg/kg. And it will be observed that the duration of the effect, at this minimal dose, is considerably greater for the d,l-glaucine hydrobromide than for the d-glaucine hydrobromide.

Comparative test 6

The equivalent effective doses for codeine phosphate and d,l-glaucine hydrobromide with oral administration were determined on 20 female guinea pigs with body weights between 230 and 600 g. The guinea pigs were divided into four groups. Each animal was then tested as described further above by subjecting the animal for 8 minutes to a 20% citric acid aerosol, the number of cough pulses produced during the 8 minutes being recorded. The average control value obtained in this way for each group of guinea pigs was calculated. After this control test each animal was given, by means of a throat probe, in a volume of 10 ml/kg, either doses of 50 or 100 mg/kg of body weight of codeine phosphate, or doses of 100 or 200 mg/kg of d,l-glaucine hydrobromide. One hour after administering the active substance, each animal was once more subjected for 8 minutes to the citric acid aerosol and the number of cough pulses recorded. The results were compared with the control values and expressed as percentages of the control values. The results are shown in Table V.

TABLE V

| Active Substance | Dose mg/kg | Cough pulses percent of control value |
|---|---|---|
| Codeine phosphate | 50 | 37 |
| | 100 | 50 |
| d,l-glaucine hydrobromide | 100 | 30 |
| | 200 | 44 |

The results show that a dose of 75 mg of codeine phosphate per kg of body weight has about the same effect as a dose of 150 mg of d,l-glaucine hydrobromide per kg of body weight.

In a further comparative test, 40 female guinea pigs with body weights between 230 and 500 g were divided into 4 groups and each animal was again subjected to the action of a 20% citric acid aerosol for 8 minutes. From the control values thus obtained the average control value for each group was calculated. Each animal of each group was then given, by means of a throat probe, either 75 mg/kg of codeine phosphate, or 135 mg/kg of d,l-glaucine hydrochloride, or 150 mg/kg of d,l-glaucine hydrobromide, or 378 mg/kg of d,l-glaucine embonate. These doses are the equimolar quantities, based on glaucine. After a period of 1, or 3, or 5, or 24 hours each animal was again subjected for 8 minutes to the action of the citric acid aerosol, and the number of cough pulses during this period was recorded. The values thus obtained were compared with the control values and the percent deviation of the average measured value for each group, from the average control value, was calculated. The results are shown in Table VI.

TABLE VI

| Active substance | Cough pulses during 8 minutes, percent of control value, after: | | | |
|---|---|---|---|---|
| | 1 h | 3 h | 5 h | 24 h |
| Codeine phosphate | 84 | 70 | 84 | 95 |
| d,l-glaucine hydrobromide | 90 | 47 | 59 | 113 |
| d,l-glaucine hydrochloride | 80 | 72 | 69 | 102 |
| d,l-glaucine embonate | 80 | 51 | 57 | 81 |

These results show that in all the tests the d,l-glaucine salts have a greater effect than codeine phosphate in reducing the number of cough pulses. In particular it will be observed that d,l-glaucine embonate has a considerably longer-lasting effect without any delay in the beginning of the effect.

Comparative test 7

The toxicity thresholds of codeine phosphate, of d-glaucine hydrobromide and of d,l-glaucine hydrobromide were determined in mice by the Wilcox method. It emerged, as shown in Table VII, that d,l-glaucine is considerably less toxic than d-glaucine. The toxicities of codeine phosphate and d,l-glaucine hydrobromide are about equal.

TABLE VIII

| Active substance | $LD_{50}$ peroral mg/kg | $LD_{50}$ subcutaneous mg/kg |
|---|---|---|
| codeine phosphate | 640 | 230 |
| d-glaucine hydrobromide | 345 | 125 |
| d,l-glaucine hydrobromide | 686 | 320 |

Comparative test 8

In order to investigate the anti-cough effectiveness of orally given codein phosphate, d-glaucine hydrobromide, d,l-glaucine hydrobromide, l-glaucine hydrobromide and l-glaucine-d-tartrate, respectively, guinea pigs were orally dosed with one of the active agents mentioned one hour before being exposed for ten minutes to a 5% active acid aerosol. In each case the last 5 minutes of the exposure were used for the measurements. The effective doses $ED_{50}$ are shown in Table IX:

TABLE IX

|  | Oral $ED_{50}$ mg/kg |
|---|---|
| Codein phosphate | 94,9 |
| d-glaucine hydrobromide | 198,96 |
| d,l-glaucine hydrobromide | 16,0 |
| l-glaucine hydrobromide | 7,21 |
| l-glaucine-d-tartrate | 6,8 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An antitussive composition comprising a pharmaceutically-acceptable carrier and from about 4 to about 99 percent by weight of a glaucine compound selected from the group consisting of l-glaucine, d,l-glaucine, the physiologically-acceptable salts thereof, and mixtures thereof.

2. Composition of claim 1 wherein the composition is in dosage unit form, containing an effective amount of from 1 to 1000 mg of said glaucine compound per dosage unit.

3. Composition of claim 2 in dosage unit form of a pill, dragee, capsule or tablet adapted for oral administration and containing about 5 to 50 mg of said glaucine compound.

4. Composition of claim 1 in liquid form adapted for oral administration and containing from 1 to 10 mg of said glaucine compound per ml liquid.

5. Composition of claim 1 wherein said composition contains l-glaucine or a physiologically-acceptable salt thereof as the sole essential antitussive agent.

6. Composition of claim 4 wherein said composition is in the form of a syrup and said glaucine compound is l-glaucine hydrobromide.

7. Composition of claim 1 wherein said composition is in dosage unit form containing an effective amount of from 1 to 1000 mg per unit of d,l-glaucine or a physiologically-acceptable salt thereof as the sole essential antitussive agent.

8. Composition of claim 2 wherein said glaucine compound is at least about 50 percent l-glaucine or a physiologically-acceptable salt thereof.

9. Composition according to claim 1 wherein said glaucine compound is l-glaucine embonate.

10. Composition according to claim 1 wherein said glaucine compound is d,l-glaucine embonate.

11. Composition according to claim 1 wherein said glaucine compound is d,l-glaucine tartrate.

12. A method of suppressing coughs, comprising administering orally to a mammal in need thereof, an antitussive effective amount of a glaucine compound selected from the group consisting of l-glaucine, d,l-glaucine, the physiologically acceptable salts thereof, and mixtures thereof.

13. Method of claim 12 wherein said glaucine compound is l-glaucine or a pharmaceutically-acceptable salt thereof.

14. Method of claim 12 wherein said glaucine compound is d,l-glaucine or a pharmaceutically-acceptable salt thereof.

15. Method of suppressing coughs comprising administering orally to a mammal a physiologically-effective amount of a composition according to claim 1 wherein from about 50 percent to 100 percent of said glaucine compound is l-glaucine or a pharmaceutically acceptable salt thereof.

16. Method of claim 15 wherein said glaucine compound is essentially l-glaucine or a pharmaceutically acceptable salt thereof.

17. Method of claim 15 wherein said glaucine compound is d,l-glaucine or a pharmaceutically acceptable salt thereof.

18. Method of claim 15 wherein said glaucine compound is essentially l-glaucine hydrobromide.

19. Method of claim 15 wherein said glaucine compound is d,l-glaucine hydrobromide.

20. Method of claim 15 wherein said compound is administered orally at a dosage rate of from about 0.01 to about 40 mg of said compound per kg of body weight.

21. Method of claim 20 wherein the dosage rate is about 0.1 to 4 mg per kg of body weight.

22. Method of claim 21 wherein said glaucine compound is d,l-glaucine.

* * * * *